(12) United States Patent
Hwang et al.

(10) Patent No.: US 9,585,862 B2
(45) Date of Patent: Mar. 7, 2017

(54) PATCH CONTAINING RIVASTIGMINE (75) Inventors: Yong-youn Hwang, Gyeonggi-do (KR); Won-Jae Choi, Seoul (KR); Jae-Sun Kim, Gyeonggi-do (KR); Won-No Youn, Seoul (KR); Yeo-Jin Park, Seoul (KR); Joon-gyo Oh, Gyeonggi-do (KR); JongSeob Im, Gyeonggi-do (KR)

(73) Assignee: SK CHEMICALS CO., LTD., Gyeonggi-do (KR)

( * ) Notice: Subject to any disclaimer, the term of this patent is extended or adjusted under 35 U.S.C. 154(b) by 0 days.

(21) Appl. No.: 14/118,985

(22) PCT Filed: May 21, 2012

(86) PCT No.: PCT/KR2012/003986
§ 371 (c)(1),
(2), (4) Date: Feb. 3, 2014

(87) PCT Pub. No.: WO2012/161489
PCT Pub. Date: Nov. 29, 2012

(65) Prior Publication Data
US 2014/0220104 A1 Aug. 7, 2014

(30) Foreign Application Priority Data
May 20, 2011 (KR) .................. 10-2011-0048068

(51) Int. Cl.
*A61F 13/00* (2006.01)
*A61K 31/325* (2006.01)
*A61L 15/44* (2006.01)
*A61L 15/58* (2006.01)
*A61K 9/70* (2006.01)
*A61K 31/27* (2006.01)

(52) U.S. Cl.
CPC .......... *A61K 31/325* (2013.01); *A61K 9/7061* (2013.01); *A61K 9/7084* (2013.01); *A61K 31/27* (2013.01); *A61L 15/44* (2013.01); *A61L 15/58* (2013.01); *A61L 2300/00* (2013.01)

(58) Field of Classification Search
CPC .... A61K 31/325; A61K 9/7061; A61K 31/27; A61K 9/7084; A61L 15/44; A61L 15/58; A61L 2300/00
See application file for complete search history.

(56) References Cited

U.S. PATENT DOCUMENTS

| | | | | |
|---|---|---|---|---|
| 3,615,727 | A * | 10/1971 | Starke .............................. | 422/33 |
| 6,335,031 | B1 | 1/2002 | Asmussen et al. ........... | 424/449 |
| 2004/0258741 | A1 | 12/2004 | Terahara et al. .............. | 424/449 |
| 2007/0259028 | A1 | 11/2007 | Ito ................. | 424/449 |
| 2010/0003313 | A1 | 1/2010 | Suzuki et al. ................ | 424/449 |
| 2010/0087768 | A1 | 4/2010 | Forlano et al. ................ | 602/48 |
| 2011/0217374 | A1 * | 9/2011 | Oh et al. ....................... | 424/468 |
| 2012/0197221 | A1 * | 8/2012 | Jang et al. ................... | 604/307 |
| 2013/0261571 | A1 * | 10/2013 | Prinz et al. ................... | 604/307 |

FOREIGN PATENT DOCUMENTS

| | | | |
|---|---|---|---|
| EP | 2172194 | 4/2010 | ............. A61K 9/70 |
| GB | 2 203 040 | 10/1988 | ............. A61K 31/27 |
| KR | 10-2010-0080681 | 7/2010 | ............. A61K 9/70 |
| WO | WO 2007/064407 | 6/2007 | ............. A61K 9/70 |
| WO | WO 2007064407 A1 * | 6/2007 | |
| WO | WO 2008/050673 | 5/2008 | .......... A61K 31/343 |
| WO | WO 2011029598 A1 * | 3/2011 | |

OTHER PUBLICATIONS

International Search Report (ISR) in PCT/KR2012/003986 dated Oct. 23, 2012 with English translation.
Written Opinion (WO) in PCT/KR2012/003986 dated Oct. 23, 2012.
Extended European Search Report dated Sep. 29, 2014.
Henkel Ltd., "Duro-Tak and Gelva Transdermal Pressure Sensitive Adhesives", Product Selection Guide, Nov. 20, 2013, 2 pages.

* cited by examiner

*Primary Examiner* — Robert A Wax
*Assistant Examiner* — Olga V Tcherkasskaya
(74) *Attorney, Agent, or Firm* — Harness, Dickey & Pierce, P.L.C.

(57) ABSTRACT

The present invention relates to a rivastigmine-containing patch having improved storage stability and proper release property.

14 Claims, 3 Drawing Sheets

PATCH CONTAINING RIVASTIGMINE

CROSS-REFERENCE TO RELATED APPLICATIONS

This application is a national phase application of PCT Application No. PCT/KR2012/003986, filed on May 21, 2012, which claims the benefit and priority to Korean Patent Application No. 10-2011-0048068 filed in the Republic of Korea on May 20, 2011, the entire disclosures of the applications identified in this paragraph are incorporated herein by references.

FIELD

The present invention relates to a patch containing rivastigmine as an effective ingredient, which has improved storage stability.

BACKGROUND

Rivastigmine, (S)-N-ethyl-3-[(1-dimethylamino)ethyl]-N-methyl-phenyl-carbamate is used for treating Alzheimer's disease, and it is useful as an acetylcholinesterase inhibitor in the central nervous system.

Such rivastigmine is commercially available in the form of a patch. GB Patent No. 2,203,040 discloses a transdermal composition in the form of a patch in Example 2, in which the patch is prepared by mixing rivastigmine with two polymers and a plasticizer to obtain a viscous composition, and applying the composition to a foil.

U.S. Pat. No. 6,335,031 discloses a composition for transdermal administration, containing rivastigmine or a salt thereof and an antioxidant as a stabilizer. According to this patent, conventional compositions for transdermal administration which contains rivastigmine are susceptible to degradation even in air-tight packaging due to oxidation by oxygen, making it difficult to secure the storage period required for commercial distribution. Accordingly, in order to solve the above problem, this patent discloses a composition for transdermal administration of rivastigmine, containing an antioxidant such as tocopherol, esters thereof, ascorbic acid, butylhydroxytoluene, butylhydroxyanisole and propyl gallate. Thus, tocopherol has been used as a stabilizer in commercially available products for transdermal administration of rivastigmine.

However, since tocopherol is susceptible to degradation by air or light, it must be kept in cold storage under an inert atmosphere, and since it is present in a liquid form, it is difficult to handle and store during commercial production. In addition, because tocopherol can act as an anticoagulant when administered in vivo, many drug-approved agencies have set a tolerable upper intake level. Therefore, in order to overcome these problems, there is still a need to develop a rivastigmine patch having improved stability.

BRIEF SUMMARY

The present invention is designed to solve the above problems, and therefore it is an object of the present invention to provide a rivastigmine-containing patch having improved stability.

Technical Solution

In order to achieve the objects as mentioned above, the present inventors have conducted various experimentations and obtained the results described in the Examples below.

First, the present inventors have obtained the following facts through their studies on a drug-containing layer.

Suitable excipients having compatibility with an active ingredient were selected with reference to compatibility test results, and observed for the permeability of the active ingredient over the concentration thereof, to recognize that the active ingredient exhibits a permeation rate (e.g., flux) equivalent to the control drug at a concentration of 15 to 35 wt %, preferably 25 to 35 wt % based on the total weight of a drug-containing adhesive layer after drying. When this prescription of such a concentration range was applied in the human skin for 24 hours, the poor adhesiveness of the patch led to the prescription moving away from the adhesion site, thereby causing dark rings on the skin in which the patch was applied. In order to improve this problem, the present inventors have made a layer for adhering to the skin that is not miscible with the active ingredient and an acryl-based adhesive and integrated the layer with a drug-containing layer, thereby developing a prescription of double layers.

Second, the present inventors have obtained the following facts through their studies on a layer for adhering to the skin.

In a prescription of double layers for a rivastigmine patch formulation, a layer (Layer 2) for adhering to the skin and using a silicon adhesive, acts as a barrier between the skin and a drug-containing adhesive layer to reduce the permeability of the active ingredient. Accordingly, the thickness of Layer 2 has a significant influence on the permeation rate of a drug into the skin. When observing the permeability of a drug depending on the thickness of Layer 2, prescriptions of a trimethylated silica treated with dimethyl siloxane having a viscosity of 1200 mPa·s, a solid content of 60%, and a peel adhesion value of 700 g/cm sold under trademark BIO-PSA™ 7-4302 (hereinafter, "Silicon Adhesive 7-4302") and a trimethylated silica treated with dimethyl siloxane having a viscosity of 800 mPa·s, a solid content of 60%, and a peel adhesion value of 90 g/cm sold under trademark BIO-PSA™ 7-4202 (hereinafter, "Silicon Adhesive 7-4202") in each amount of 30 mg/10 cm$^2$ based on the each dry weight thereof in the layer for adhering to the skin exhibit drug permeability equivalent to the control drug. In order to select the better of the two prescriptions, adhesives used were compared for their adhesiveness and as a result, a prescription of Silicon Adhesive 7-4302, similar to the control drug, in an amount of 20 mg/10 cm$^2$ to 40 mg/10 cm$^2$, preferably 27 mg/10 cm$^2$ to 33 mg/10 cm$^2$, more preferably about 30 mg/10 cm$^2$ was adopted as being favorable in the present invention.

Third, the present inventors have obtained the following facts through their studies on a polymer to be used.

Rivastigmine free base which is used as an active ingredient in the rivastigmine patch is present in a liquid form at room temperature, and when it is present in an amount of 30 wt % or more in a drug-containing adhesive layer after drying, a thickening polymer must be used together. Accordingly, the present inventors have made studies to determine the amount of a polymer which can provide drug permeability equivalent to the control drug, the used polymer being a copolymer comprising butyl methacrylate and methyl methacrylate having a weight average molecular weight of about 150,000 g/mol sold under the trademark PLASTOID B (hereinafter, "Copolymer B") having compatibility with the active ingredient. Specifically, when conducting experimentations for determining the amount of the polymer by controlling the range to be 10 to 30 wt % based on the total weight of the drug-containing adhesive layer after drying, results showed that the more the amount of polymer is used, the less the drug permeability is obtained.

This is expected because the increase of the polymer amount raises viscosity to hinder the drug from being diffused, but the present invention is not limited to this theoretical presumption. Also, a prescription in which the polymer is used in an amount of 20 wt % based on the total weight of the drug-containing adhesive layer after drying was confirmed to provide the most similar drug permeability as compared to the control drug.

Fourth, among several prescriptions of the present invention adopted through the formulation studies, the most preferred prescription is shown in Table 1.

TABLE 1

| | Drug-containing Adhesive Layer | Layer for Adhering to the Skin |
|---|---|---|
| Rivastigmine in free base | 25~35% (preferably 30%) | Silicon Adhesive 7-4302 (20~40 mg/10 cm², preferably 30 mg/10 cm²) |
| Copolymer B | 16~24% (preferably 20%) | |
| Solvent | Adequate amount | |
| Adhesive 87-235A | 45~55% (preferably 50%) | |

The solvent listed in Table 1 was removed during a drying process. The content of each ingredient listed in Table 1 means a dry weight thereof. That is, products of the adhesive comprising a random copolymer of 58 to 66 parts by weight of 2-ethylhexyl acrylate, 28 to 36 parts by weight of methyl acrylate and 4 to 8 parts by weight of acrylic acid, having a solids content of 36.5%, a Brookfield viscosity (22° C., #5, 20 rpm) of 8000 mPa·s, a theoretical Tg value of −35° C., a density of 0.92 g/ml, and a solvent composition comprising 87% ethyl acetate and 13% hexane sold under the trademark DUROTAK 87-235A (herein, "Adhesive 87-235A") and Silicon Adhesive 7-4302 themselves comprise a certain amount of a solvent, and in Table 1, each content of such products is represented by a numerical value excluding the amount of the solvent.

Rivastigmine patches, which were prepared according to the final prescription adopted, were applied in a membrane and a human cadaver skin for 72 hours, and then compared with the control drug for their permeation rate (e.g., flux). The results showed that the rivastigmine patches exhibit similar effects.

Fifth, the present inventors have obtained the following facts through their studies for the adoption of packaging conditions.

In order to adopt packaging conditions which allow storage stability of rivastigmine patches, a severe stability test has been conducted. Specifically, the stability of rivastigmine patches was evaluated under severe conditions of atmosphere packaging and nitrogen packaging. As a result, it was confirmed that the packaging by nitrogen filling allows the formation of less flexible substances (impurities).

Thus, the present inventors have endeavored to develop a rivastigmine patch having the desired characteristics without using a stabilizer such as tocopherol which may cause several problems, and found that the stability and suitable release of rivastigmine can be achieved by properly adopting an adhesive and a polymer used in a rivastigmine-containing layer and controlling the amount thereof in a certain ratio, and applying a proper packaging method for the rivastigmine patch.

DETAILED DESCRIPTION

Accordingly, the present invention provides a rivastigmine-containing patch, containing double layers of:

(a) a drug-containing adhesive layer obtained by using rivastigmine free base, a copolymer of butyl methacylate and methyl methacylate, and an adhesive; and (b) a layer for adhering to the skin, comprising a silicon adhesive, wherein the adhesive in the drug-containing adhesive layer is a random copolymer of 58 to 66 parts by weight of 2-ethylhexyl acrylate, 28 to 36 parts by weight of methyl acrylate and 4 to 8 parts by weight of acrylic acid. More preferably, as the adhesive in the drug-containing adhesive layer, Adhesive 87-235A is used.

More preferably, the copolymer of butyl methacrylate and methyl methacrylate is a random copolymer thereof, and has a weight average molecular weight of 130,000-170,000 g/mol, most preferably, Copolymer B.

In the present invention, as the silicon adhesive, trimethylated silica treated with dimethyl siloxane is more preferably used, most preferably is Silicon Adhesive 7-4302.

The amount of such a silicon adhesive has great influence on the release of rivastigmine, and according to experimentation results, it is preferred that Silicon Adhesive 7-4302 is used in an amount of 27 mg/10 cm² to 33 mg/10 cm² based on the dry weight thereof. Most preferably, Silicon Adhesive 7-4302 is applied in an amount of about 30 mg/10 cm² based on the dry weight thereof.

Also, the present invention provides a rivastigmine-containing patch, containing double layers of:

(a) a drug-containing adhesive layer obtained by using substantially only rivastigmine free base, Copolymer B, and Adhesive 87-235A; and (b) a layer for adhering to the skin, obtained by using substantially only solid contents of Silicon Adhesive 7-4302.

The term "substantially" used herein refers to the inclusion of a component (particularly, an antioxidant such as tocopherol) other than the above-mentioned ingredients in an amount of 1 wt % or less, preferably 0.5 wt %, more preferably 0.1 wt %, most preferably 0.05 wt %.

In the rivastigmine-containing patch of the present invention, it is preferred that the drug-containing adhesive layer consists of 25 to 35 wt % of rivastigmine free base; 16 to 24 wt % of a copolymer of butyl methacrylate and methyl methacrylate (preferably Copolymer B); and 45 to 55 wt % of a random copolymer (preferably solid contents of Adhesive 87-235A) of 58 to 66 parts by weight of 2-ethylhexyl acrylate, 28 to 36 parts by weight of methyl acrylate and 4 to 8 parts by weight of acrylic acid, based on the total weight of the drug-containing adhesive layer, and the layer for adhering to the skin is made of trimethylated silica treated with dimethyl siloxane (preferably solid contends of Silicon Adhesive 7-4302) in an amount of 27 mg/10 cm² to 33 mg/10 cm² (more preferably 30 mg/10 cm²) based on the dry weight thereof.

Further, the present invention provides a method for preparing a rivastigmine free base-containing patch, containing:

(a) mixing rivastigmine free base; a copolymer of butyl methacrylate and methyl methacrylate (preferably Copolymer B); a random copolymer (preferably solid contents of Adhesive 87-235A) of 58 to 66 parts by weight of 2-ethylhexyl acrylate, 28 to 36 parts by weight of methyl acrylate and 4 to 8 parts by weight of acrylic acid; and a solvent, to form a drug-containing adhesive layer consisting of 25 to 35 wt % of the rivastigmine free base; 16 to 24 wt % of the copolymer of butyl methacrylate and methyl methacrylate; and 45 to 55 wt % of the random copolymer based on the total dry weight of the drug-containing adhesive layer, and (b) forming a layer for adhering to the skin, the layer having trimethylated silica treated with dimethyl siloxane (preferably solid contends of Silicon Adhesive 7-4302) in an amount of 27 mg/10 cm² to 33 mg/10 cm² (more preferably 30 mg/10 cm²) based on the dry weight thereof.

In the above-mentioned method, step (b) may be carried out before or after step (a). Alternatively, steps (a) and (b) may also be simultaneously carried out.

In the case of such a patch consisting of double layers, the release of the active ingredient may significantly vary depending on the presence of any other components in the drug-containing adhesive layer/the layer for adhering to the skin and a mixing ratio of the components, and thus the amount of additives and each component should be controlled accurately.

A dosage of the rivastigmine patch of the present invention may vary depending on the age, weight, sex and body condition of the patient, and the severity of the patient's symptoms. Commercially available products for transdermal administration of rivastigmine which are used for treating Alzheimer's dementia and Parkinson's dementia have a typical dosage ranging from 9 mg to 18 mg, and may be administered to the skin once a day.

Advantageous Effects

The rivastigmine patch of the present invention has excellent stability and exhibits a proper release pattern.

DESCRIPTION OF DRAWINGS

Other objects and aspects of the present invention will become apparent from the following descriptions of the embodiments with reference to the accompanying drawings in which.

EXAMPLES

Hereinafter, various preferred examples of the present invention will be described in detail for better understanding. However, the examples of the present invention may be modified in various ways, and they should not be interpreted as limiting the scope of the invention. The examples of the present invention are just for better understanding of the invention to persons having ordinary skill in the art.

Example 1

Study on Adhesive

In order to develop a rivastigmine patch using rivastigmine free base as an active ingredient, the following experimentations for finding out a suitable adhesive were conducted.

Adoption of Kind of Adhesive

In order to adopt a suitable adhesive for preparing a rivastigmine patch, each of various adhesives was mixed with rivastigmine free base to confirm the appearance, miscibility and compatibility thereof.

For a compatibility test, ten adhesives were used as a candidate material, considering the kind of a polymer and functional group present in the composition of each adhesive, the presence of a crosslinker and a solvent present in the composition. Details of the ten adhesives are shown in Table 2, wherein each product listed under the column "Product name" is an adhesive sold under the respective listed trademark.

TABLE 2

| Product name | Polymer | Functional group | Cross-linker | Solvent |
|---|---|---|---|---|
| DURO-TAK™ 87-202A | Acrylic | —OH | ○ | EA, IPA, MeOH |
| DURO-TAK™ 87-2510 | Acrylic | —OH | X | EA, Heptane |
| DURO-TAK™ 87-2852 | Acrylic | —COOH | ○ | EA, IPA, Hexane, Toluene |
| DURO-TAK™ 87-9088 | Acrylic | None | Not applicable | EA |
| DURO-TAK™ 87-235A | Acrylic | —COOH | X | EA, Heptane |
| DURO-TAK™ 87-2516 | Acrylate-vinylacetate | —OH | ○ | EA, EtOH, Heptane, MeOH |
| DURO-TAK™ 87-4287 | Acrylate-vinylacetate | —OH | X | EA |
| DURO-TAK™ 87-2052 | Acrylate-vinylacetate | —COOH | ○ | EA, IPA, EtOH, Heptane |
| DURO-TAK™ 87-4098 | Acrylate-vinylacetate | None | Not applicable | EA |
| DURO-TAK™ 87-2051 | Acrylate-vinylacetate | —COOH | X | EA, Heptane |

In Table 2, EA refers to ethyl acetate, IPA refers to 2-propanol, MeOH refers to methanol, and EtOH refers to ethanol.

Specifically, adhesives containing an acryl- or acrylate-vinylate-based polymer and having no functional group or a hydroxyl or carboxyl group were used. Also, the presence of a crosslinker in the adhesives was evaluated as an important factor to show a compatibility difference. The appearance and miscibility of each adhesive are shown in Table 3, wherein each "Durotak" listed under the column "Ingredient" is a different adhesive sold under the respective trademark.

TABLE 3

| | | Appearance | | Miscibility | | Total impurity (% impurity) | |
|---|---|---|---|---|---|---|---|
| No. | Ingredient | Initial | 2 wks | Initial | 2 wks | Initial | 2 wks |
| 1 | Rivastigmine base | Slightly yellow | Slightly yellow | ○ | ○ | 0.03 | 0.07 |
| 2 | Rivastigmine base/Durotak 87-202A | Colourless | Yellow | ○ | ○ | 0.04 | 0.45 |
| 3 | Rivastigmine base/Durotak 87-2510 | Slightly yellow | Slightly yellow | ○ | ○ | 0.03 | 0.26 |
| 4 | Rivastigmine base/Durotak 87-2852 | Slightly yellow | Brown | ○ | ○ | 0.02 | 2.61 |

TABLE 3-continued

| No. | Ingredient | Appearance | | Miscibility | | Total impurity (% impurity) | |
|---|---|---|---|---|---|---|---|
| | | Initial | 2 wks | Initial | 2 wks | Initial | 2 wks |
| 5 | Rivastigmine base/Durotak 87-9088 | Slightly yellow | Slightly yellow | ○ | ○ | 0.10 | 9.48 |
| 6 | Rivastigmine base/Durotak 87-235A | Colourless | Colourless | ○ | ○ | 0.04 | 0.11 |
| 7 | Rivastigmine base/Durotak 87-2516 | Slightly yellow | Brown | ○ | ○ | 0.03 | 0.70 |
| 8 | Rivastigmine base/Durotak 87-4287 | Colourless | Slightly yellow | ○ | ○ | 0.40 | 0.25 |
| 9 | Rivastigmine base/Durotak 87-2052 | Slightly yellow | Brown | ○ | ○ | 0.11 | 4.34 |
| 10 | Rivastigmine base/Durotak 87-4098 | Slightly yellow | Slightly yellow | X | X | 0.46 | 0.49 |
| 11 | Rivastigmine base/Durotak 87-2051 | Slightly yellow | Slightly yellow | ○ | ○ | 0.22 | 0.22 |

As shown in Table 3, mixtures of the active ingredient and each adhesive were observed for their properties for 2 weeks, and as a result, adhesives that were colorless or slightly yellow in the initial mixing state changed to yellow and then to brown. For example, in the case that the adhesive sold under the trademark DUROTAK 87-202A was used, the color changed to yellow, while in the cases that the adhesives sold under the trademarks DUROTAK 87-2852, 87-2516 and 87-2052 were used, the color changed to brown. The adhesives undergoing a significant color change were commonly confirmed to have a crosslinker. In the case that the adhesive sold under the trademark DUROTAK 87-4287 was used, the color changed from being colorless to slightly yellow. The miscibility between the active ingredient and each adhesive was observed to be suitable in all cases, except of the case using the adhesive sold under the trademark DUROTAK 87-4098.

From these results, it was confirmed that the adhesives of case 3 and 6, i.e., the adhesives sold under the trademarks DUROTAK 87-2510 and 87-235A, can be suitably used together with the active ingredient of rivastigmine patches. On comparing a generation degree of flexible substances (impurities) from the two adhesives, Adhesive 87-235A was confirmed to form a more stable mixture with the active ingredient. Accordingly, Adhesive 87-235A was adopted as an adhesive for use in the development of the rivastigmine patch of the present invention, and was also used in further experimentations.

Adoption of Relative Amount of Adhesive

Adhesive 87-235A adopted in the above preformulation experimentation was used as an adhesive to study a prescription of a rivastigmine patch formulation which can exhibit a drug permeability equivalent to the control drug sold under the trademark EXELON. Since rivastigmine free base is present in a liquid form at room temperature, when it is present in an amount of 30 wt % or more in a drug-containing adhesive layer in the preparation of a patch formulation, a thickening polymer must be used together. For this reason, as such a polymer, Copolymer B having compatibility with the active ingredient was used. In order to adopt an amount of the active ingredient, relative to other ingredients, capable of exhibiting a drug permeability equivalent to the control drug, the weight ratio of the active ingredient and the polymer was set to 3:2, and then an amount of the adhesive was controlled to determine the weight ratio of ingredients in the drug-containing adhesive layer.

Prescriptions using Adhesive 87-235A as an adhesive and Copolymer B as a polymer with reference to the results of the previous preformulation experimentation were made with varying the weight ratio of the active ingredient and the adhesive, as shown in Table 4. Meanwhile, experimentation for optimizing an amount of the polymer will be described in the next step.

TABLE 4

| Sample | API (active pharmaceutical ingredient) | Polymer | Adhesive (Solid Contents 36.5%) |
|---|---|---|---|
| I100526-1 | 15 wt % | 10 wt % | 75 wt % |
| I100526-2 | 30 wt % | 20 wt % | 50 wt % |
| I100526-3 | 45 wt % | 30 wt % | 25 wt % |

Patches were prepared according to such prescriptions and used in a test for confirming drug permeability to the skin. All patches prepared by such prescription contained the active ingredient in an amount of 18 mg/10 cm$^2$. The test for drug permeability to the skin was conducted under the conditions shown in Table 5, and the results thereof are shown in FIG. 1

TABLE 5

| Membrane | Ethylene-vinyl acetate (EVA) film (CoTran 9715) |
|---|---|
| Cell type | Vertical Franz cell (7 mL) |
| Receptor medium | pH 7.4 Phosphate buffer |
| Medium temperature | 32.0 ± 0.5° C. |
| Stirring Rate | 300 rpm |
| Application area | 1 cm$^2$ |
| Sampling volume | 2 mL including 1.4 mL of discard volume |
| Medium replacement | 2 mL of medium stored at 32° C. |
| Sampling time | 1, 2, 3, 6, 9, 12, 18, 24, 30, 36, 48 hrs |

Figure 1:
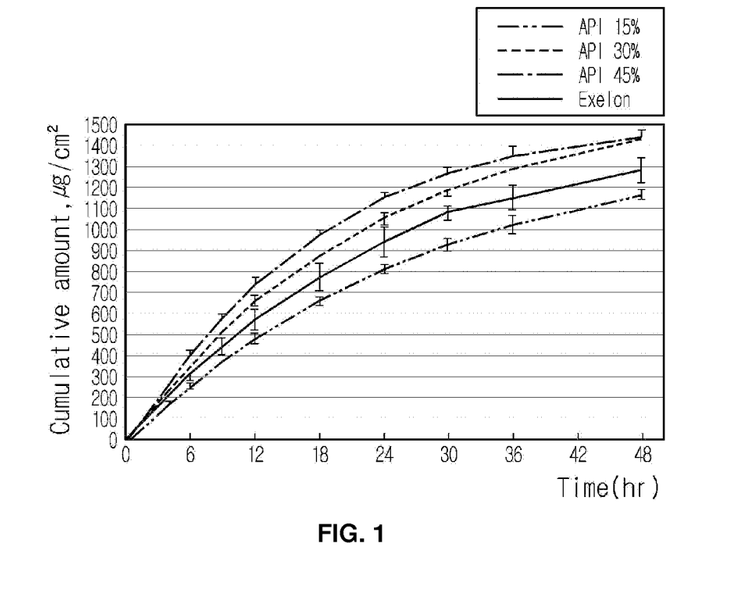
FIG. 1 shows the permeability of the active drug to the skin, obtained from experimentations for adopting the desired ratio of an adhesive.

As can be seen in FIG. 1, the higher the concentration the active ingredient was, the more the drug permeability was obtained. Also, when the concentration of the active ingredient ranges from 15 to 30 wt %, a permeation rate (e.g. flux) of the drug equivalent to the control drug sold under the trademark was obtained. Based on this matter, in order to find out prescriptions capable of exhibiting a drug permeability equivalent to the control drug, a further experimentation was processed by controlling the relative amount of the active ingredient relative to other components and modifying the adhesive by taking into consideration the adhesiveness of the drug-containing adhesive layer and the cold flow generation thereof, as illustrated below.

Evaluation of Adhesiveness and Cold Flow of Drug-Containing Adhesive Layer

Prescriptions of rivastigmine patch formulations obtained above were applied in the human skin for 24 hours so as to evaluate the adhesiveness and cold flow of a drug-containing adhesive layer. When such prescription was applied in the human skin for 24 hours, the poor adhesiveness of the patch led to the prescription moving away from the adhesion site, thereby causing dark rings. This was expected because the active ingredient, rivastigmine free base of the patches is present in a liquid form at room temperature, from which a mixture of the liquid active ingredient and the adhesive becomes reduced in terms of adhesiveness, and the patches move away from the adhesion site due to the poor adhesiveness of the patch formulation, to cause dark rings. In order to improve this problem, a layer for adhering to the skin that is not miscible with the active ingredient and an acryl-based adhesive were made, followed by integrating the layer with a drug-containing layer, thereby developing a prescription of double layers, as illustrated below.

Example 2

Study on Layer for Adhering to Skin

Adoption of Kind of Adhesive Used in Layer for Adhering to Skin

Prescriptions of a drug-containing adhesive layer, which were adopted through the above studies on various drug-containing layers, were used in studying a layer for adhering to the skin. In rivastigmine patch formulations, the layer for adhering to the skin should be maintained as a layer separated from the drug-containing adhesive layer. For this reason, the layer for adhering to the skin should not be miscible with an acryl-based adhesive which may be used as the adhesive of the drug-containing adhesive layer. If the active ingredient of a rivastigmine patch has good miscibility with the layer for adhering to the skin thereof, the drug of the drug-containing adhesive layer may diffuse into the layer for adhering to the skin by concentration gradient, thereby affecting the adhesiveness of the layer for adhering to the skin. Therefore, the active ingredient should not be miscible with the adhesive of the layer for adhering to the skin. In order to adopt the kinds of an adhesive satisfying such a condition, various adhesives including silicone-based, rubber-based and polyisobutylene-based adhesives were evaluated for their miscibility with the active ingredient. As a result, the rubber-based and polyisobutylene-based adhesives were observed to have good miscibility with the active ingredient, while the silicone-based adhesives were observed to be separated due to their poor miscibility with the active ingredient. Each adhesive was applied in a film so that its thickness became 50 μm after drying, and attached to the human skin for 24 hours, so as to evaluate a degree of generation of a cold flow. The evaluation was conducted by attaching each patch to the brachial site of ten subjects, rating a degree of generation of dark rings due to a cold flow based on 0 to 5 scores, and calculating an average of the obtained scores. The rating for the adhesiveness of each adhesive was specifically made on the adhering state of each patch, a degree of generation of dark rings, adhesiveness strength as shown in Table 6.

The results for the miscibility of each adhesive and a degree of generation of dark rings according to adhesiveness are shown in Table 7, wherein "DURO-TAK 87-235A" is Adhesive 87-235A and the remaining listed "DURO-TAK" products are different adhesives sold under the respective trademarks, and wherein "Bio PSA 7-4302" is Silicon Adhesive 7-4302.

TABLE 7

|  | Acryl adhesive[1] | Rubber adhisive[2] | PIB Adhesive[3] | Silicone adhiesive[4] | Control drug |
|---|---|---|---|---|---|
| Miscibility with Acryl adhesive | ○ | Δ | Δ | X | — |
| Miscibility with Active Ingredient | ○ | ○ | ○ | X | — |
| Adhering State | 0.4 | 2.2 | 2.1 | 0.4 | 0.4 |
| Dark rings | 3.4 | 3.1 | 3.1 | 2.1 | 2.3 |
| Adhesiveness Strength | 2.6 | 1.6 | 1.6 | 2.5 | 2.4 |

[1] DURO-TAK 87-235A,
[2] DURO-TAK 87-611A,
[3] DURO-TAK 87-608A, and
[4] Bio PSA 7-4302

As can be seen from the above results, when using the silicon-based adhesive, dark rings were observed in a degree equivalent to or less than that of the control drug, while when using the rubber-based and polyisobutylene-based adhesives, dark rings were observed in a degree equivalent to or more than that of the case using the conventional acryl-based adhesive.

Based on these matters, it was concluded that the rubber-based and polyisobutylene-based adhesives cannot be used in the layer for adhering to the skin since they have a certain degree of miscibility with acryl-based adhesives and the active ingredient of a rivastigmine patch, while the silicon-based adhesive not miscible with the acryl-based adhesives and the active ingredient can be used in the layer for adhering to the skin, thereby minimizing the generation of a cold flow.

Prescription of Layer for Adhering to the Skin

In a prescription of double layers for a rivastigmine patch formulation, a layer (Layer 2) for adhering to the skin and using a silicone adhesive acts as a barrier between the skin and a drug-containing adhesive layer to reduce the permeability of the active ingredient. Accordingly, it is expected that the thickness of Layer 2 has a significant influence on the permeation rate of a drug into the skin. Based on this matter, a patch of double layers was prepared by varying the amount of an adhesive per unit area and the drug permeability thereof to the skin was observed. The drug-containing adhesive layer of the patch was obtained by prescription 1100526-2 (refer to Table 4) which was used in the studies on a drug-containing layer (Layer 1), the layer for adhering to the skin was obtained by applying each of three silicon-based adhesives in various thicknesses, and the two layers were integrated, and then used in studies for achieving a drug permeability to the skin equivalent to the control drug.

TABLE 6

| Evaluation Items | 0 | 1 | 2 | 3 | 4 | 5 |
|---|---|---|---|---|---|---|
| Adhering State | wholly adhered | very slightly unstuck at edge parts | slightly unstuck at edge parts | significantly unstuck at edge parts | about half detached | completely detached |
| Dark Rings | all areas being clear | Presence of dark rings in 1/4 parts of the areas | Presence of dark rings in 2/4 parts of the areas | Presence of dark rings in 3/4 parts of the areas | Presence of dark rings in all areas | Presence of thick circular dark rings |
| Adhesiveness Strength | very slightly weak | slightly weak | moderate | very slightly strong | slightly strong | very strong |

TABLE 8

| Samples | Drug-containing Adhesive Layer | Adhesive used in Layer for Adhering to the Skin | Amount of Adhesive in Layer for Adhering to the Skin (mg/10 cm$^2$) |
|---|---|---|---|
| I100531-1 | Rivastigimine base 30% Copolymer B 20%, Adhesive 87-235A 50% | Silicon adhesive sold under trademark BIO-PSA 7-4202 | 30 |
| I100531-2 | | | 60 |
| I100531-3 | | Silicon Adhesive 7-4202 | 30 |
| I100531-4 | | | 60 |
| I100531-5 | | Silicon Adhesive 7-4302 | 30 |
| I100531-6 | | | 60 |

The thickness of the layer for adhering to the skin was controlled by adjusting the weight of the silicon-based adhesive per unit area. For example, the thickness of the layer for adhering to the skin was 30 μm when the silicon-based adhesive is present in an amount of 30 mg/10 cm$^2$, and the thickness of the layer for adhering to the skin was 60 μm when the silicon-based adhesive is present in an amount of 60 mg/10 cm$^2$. The results of a drug permeability to the skin after each prescription was made for 48 hours are shown in FIG. 2.

Figure 2:
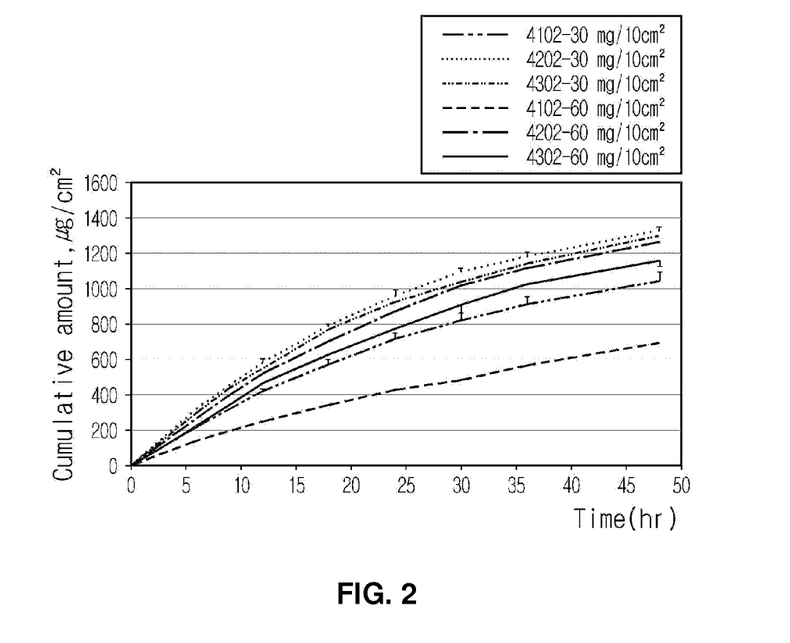
FIG. 2 shows the permeability of the active drug to the skin, obtained from experimentations for adopting the desired prescription of a layer for adhering to the skin.

As can be seen in FIG. 2, it was confirmed through all prescriptions that a barrier between the skin and the drug became thick as the thickness of the layer for adhering to the skin increased, thereby reducing the permeability of the drug. Also, it was confirmed that the use of Silicon Adhesive 7-4202 in an amount of 30 mg/10 cm$^2$ and the use of Silicon Adhesive 7-4302 in an amount of 30 mg/10 cm$^2$ provided a drug permeability equivalent to the control drug.

Example 3

Study on Polymer

The active ingredient of a rivastigmine patch, rivastigmine free base was observed to be apt to flow down, without maintaining a certain thickness, due to its liquid properties, during the preparation of the rivastigmine patch. By such a phenomenon, the application thickness of a drug-containing mixture becomes unstable, making it difficult to maintain a certain amount of the active ingredient after drying. In this regard, a polymer capable of being used as a thickener and a film former was added to prescriptions for the purpose of gaining a viscosity suitable for applying the mixture. In order to adopt a polymer suitable for preparing a rivastigmine patch, various kinds of polymers were evaluated for their compatibility with a rivastigmine free base. As a result, it was confirmed that Plastoid B was proper in terms of appearance, miscibility and compatibility through the previous studies. Accordingly, the adopted Plastoid B was used in prescriptions to find out a suitable relative amount of the polymer.

The polymer adopted in the previous preformulation studies for a rivastigmine patch formulation was used to find out a prescription capable of providing a drug permeability equivalent to the control drug. Since the active ingredient of a rivastigmine patch, rivastigmine free base, is present in a liquid form at room temperature, a thickening polymer must be added when the amount of the active ingredient in the prescription is 30 wt % or more. Accordingly, Copolymer B was used as a polymer, as it has good compatibility with the active ingredient. In order to find out the relative amount of the polymer which can provide a drug permeability equivalent to the control drug, the weight ratio of the active ingredient and the adhesive in a drug-containing adhesive layer (Layer 1) was set to 3:5 with referent to the studies for adopting the relative amount of the adhesive, and the amount of the polymer was controlled in the range of 10 to 30 wt %. Thereby, experimentations for adopting the relative amount of the polymer were conducted. In the experimentations, a layer (Layer 2) for adhering to the skin was prescribed by using Silicon Adhesive 7-4302 in an amount of 30 mg/10 cm$^2$ (based on the dry weight thereof). Thus, prescriptions were made with varying the relative amount of the polymer as shown in Table 9.

TABLE 9

| Samples | API | Polymer | 87-235A | Layer for Adhering to the Skin |
|---|---|---|---|---|
| I100614-1 | 33.75 wt % | 10 wt % | 56.25 wt % | 4302 (30 mg/10 cm$^2$) |
| I100614-2 | 30 wt % | 20 wt % | 50 wt % | 4302 (30 mg/10 cm$^2$) |
| I100614-3 | 26.25 wt % | 30 wt % | 43.75 wt % | 4302 (30 mg/10 cm$^2$) |

The above prescriptions were applied to prepare patches, and tested for drug permeability to the skin. By such prescription, all patches were prepared such that the active ingredient is present in an amount of 18 mg/10 cm$^2$. If the amount of the active ingredient does not satisfy such numerical value in the procedure of adapting the weight ratio relative to the polymer, the amount of the active ingredient was compensated and then reflected to the test results of permeation rate (e.g., flux). Meanwhile, there is no prescription of the polymer in an amount higher than 30 wt % since 30 wt % of the polymer increased the viscosity of the mixture to cause poor application properties. A drug permeability to the skin was observed for 48 hours, and the results thereof are shown in FIG. 3.

Figure 3:
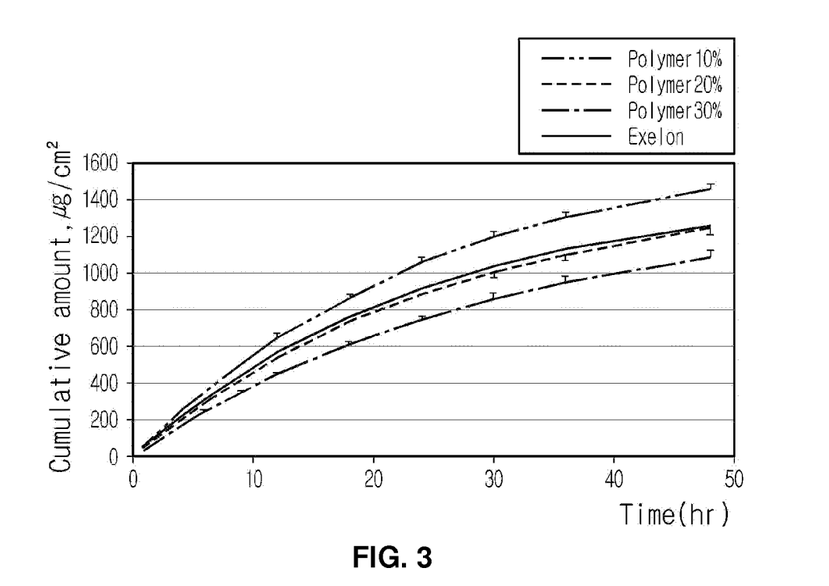
FIG. 3 shows the permeability of the active drug to the skin, obtained from experimentations for adopting the desired polymer.

As shown in FIG. 3, the more the amount of the polymer was, the less the permeability was obtained. This is expected because a viscosity is raised as the amount of the polymer increases and the increased viscosity hinders the drug from being diffused and released. Also, the prescription of 1100614-2 (refer to Table 9) which contains 20% of the polymer was confirmed to provide a drug permeability being most similar to the control drug.

Example 4

Adoption of Final Prescription

From the above Examples illustrating the results of formulation studies for a rivastigmine patch, the prescription as shown in Table 10 was adopted to most suitably prepare a rivastigmine-containing patch according to the present invention.

TABLE 10

| Drug-containing Adhesive Layer | | Layer for Adhering to the Skin |
|---|---|---|
| Rivastigmine base | 30 wt % | Silicon Adhesive 7-4302 (30 mg/10 cm$^2$, based on the dry weight) |
| Copolymer B | 20 wt % | |
| Ethyl acetate | Adequate amount[1] | |
| Adhesive 87-235A | 50 wt % | |

[1]The solvent was removed during a drying process. All wt % indicated in this Table refer to a wt % after drying.

The adopted final prescription was used to prepare rivastigmine patch samples, and the patch samples were each applied in a membrane and a human cadaver skin for 72 hours, and compared with the control drug for their permeation rate (e.g., flux). The results thereof are shown in FIG. 4 (membrane) and FIG. 5 (human cadaver skin).

Figure 4:
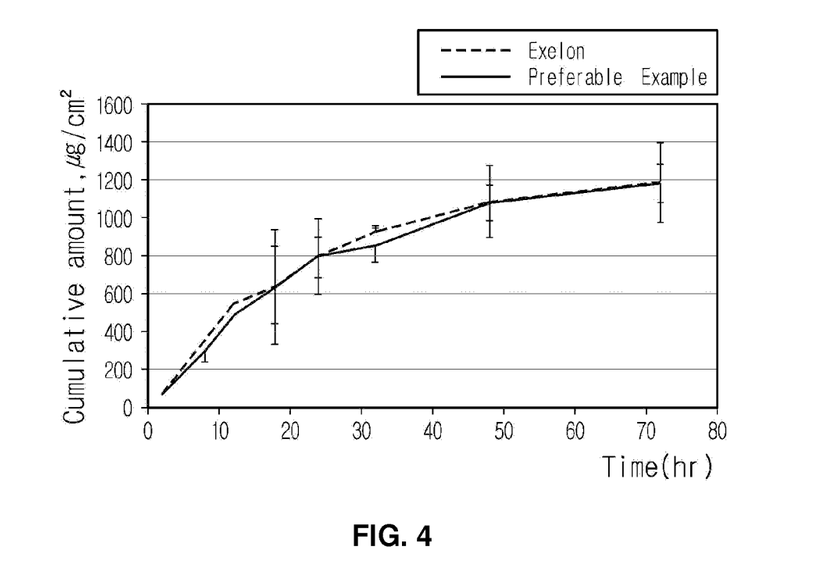
FIG. 4 shows the permeability of the active drug to the skin when the most preferred prescription according to the present invention is applied in a membrane.
Figure 5:
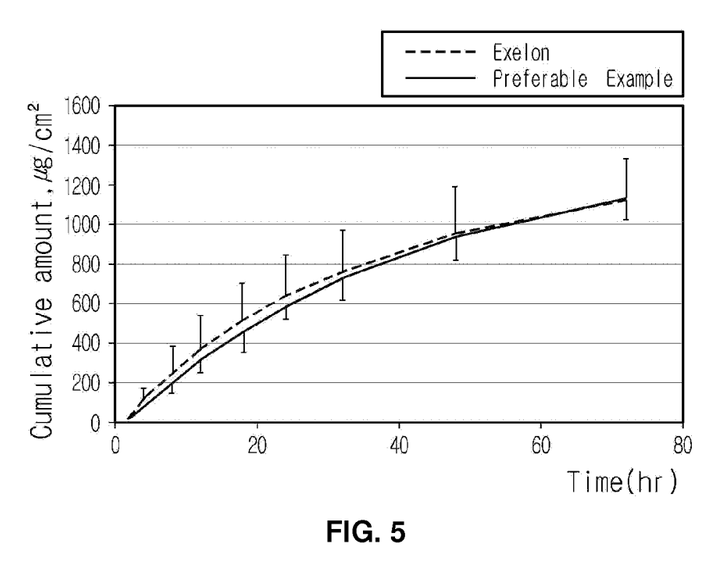
FIG. 5 shows the permeability of the active drug to the skin when the most preferred prescription according to the present invention is applied in a human cadaver skin.

As shown in FIGS. 4 and 5, the rivastigmine patch of the present invention prepared by the prescription adopted through the above formulation studies exhibited drug permeability levels equivalent to the control drug in both membrane and a human cadaver skin.

Example 5

Test for Adopting Packaging Conditions

In order to find out packaging conditions suitable in the storage stability of a rivastigmine patch, a stability test in severe conditions was conducted. In this test, an aluminum pouch and a polyacrylonitrile sachet were used as a packaging material.

Specifically, in order to confirm an effect of oxygen present in an atmosphere on a patch formulation, the stability test in severe conditions was conducted under both conditions of atmosphere packaging and nitrogen packaging, from which the stability of the rivastigmine patch according to the present invention was evaluated, and the results thereof are shown in Table 11.

TABLE 11

| Packaging Material | Packaging Condition | Amount (%) Initial | Amount (%) 1 week in severe conditions | Total Flexible substance (Impurities) (%) Initial | Total Flexible substance (Impurities) (%) 1 week in severe conditions |
|---|---|---|---|---|---|
| Aluminum Pouch | Atmosphere | 104.5 | 99.8 | 0.10 | 0.22 |
| | Nitrogen | | 99.1 | | 0.13 |
| Polyacrylonitrile (PAN) Sachet | Atmosphere | | 103.3 | | 0.17 |
| | Nitrogen | | 100.8 | | 0.14 |

As can be seen from the above results, when the rivastigmine patch was packaged by way of nitrogen filling, the least flexible substance was produced. Based on this matter, the condition suitable for packaging a rivastigmine patch was determined.

What is claimed is:

1. A rivastigmine-containing patch, comprising:
   (a) a drug-containing adhesive layer comprising rivastigmine free base, a copolymer of butyl methacrylate and methyl methacrylate, and an adhesive; and
   (b) a layer for adhering to the skin comprising a silicon adhesive,
   wherein the adhesive in the drug-containing adhesive layer is a random copolymer of 58 to 66 parts by weight of 2-ethylhexyl acrylate, 28 to 36 parts by weight of methyl acrylate and 4 to 8 parts by weight of acrylic acid, and
   wherein the drug-containing adhesive layer and the layer for adhering to the skin do not contain tocopherol.

2. The rivastigmine-containing patch of claim 1, wherein the adhesive in the drug-containing adhesive layer has a solids content of 36.5%, a Brookfield viscosity value of 8000 mPa·s, a density of 0.92 g/ml, and a solvent composition comprising 87% ethyl acetate and 13% hexane.

3. The rivastigmine-containing patch of claim 1, wherein the copolymer of butyl methacrylate and methyl methacrylate is a random copolymer thereof, and has a weight average molecular weight of 130,000 g/mol to 170,000 g/mol.

4. The rivastigmine-containing patch of claim 3, wherein the copolymer of butyl methacrylate and methyl methacrylate has a weight average molecular weight of about 150,000 g/mol.

5. The rivastigmine-containing patch of claim 1, wherein the silicon adhesive is trimethylated silica treated with dimethyl siloxane.

6. The rivastigmine-containing patch of claim 5, wherein the silicon adhesive has a viscosity of 1200 mPa·s, a solid content of 60%, and a peel adhesion value of 700 g/cm.

7. The rivastigmine-containing patch of claim 6, wherein the silicon adhesive is used in an amount of 27 mg/10 cm$^2$ to 33 mg/10 cm$^2$ based on the dry weight of the layer for adhering to the skin.

8. A product comprising a rivastigmine-containing patch, wherein the rivastigmine-containing patch of claim 1 is packaged by nitrogen filling.

9. A product comprising a rivastigmine-containing patch, wherein the rivastigmine-containing patch of claim 3 is packaged by nitrogen filling.

10. A product comprising a rivastigmine-containing patch, wherein the rivastigmine-containing patch of claim 5 is packaged by nitrogen filling.

11. A product comprising a rivastigmine-containing patch, wherein the rivastigmine-containing patch of claim 7 is packaged by nitrogen filling.

12. The rivastigmine-containing patch of claim 1, wherein the adhesive in the drug-containing adhesive layer has a solids content of 36.5%, a Brookfield viscosity value of 8000 mPa·s, a density of 0.92 g/ml, and a solvent composition comprising 87% ethyl acetate and 13% hexane,
   wherein the copolymer of butyl methacrylate and methyl methacrylate is a random copolymer thereof, and has a weight average molecular weight of 130,000 g/mol to 170,000 g/mol, and
   wherein the silicon adhesive is trimethylated silica treated with dimethyl siloxane.

13. The rivastigmine-containing patch of claim 12, wherein the silicon adhesive has a viscosity of 1200 mPa·s, a solid content of 60%, and a peel adhesion value of 700 g/cm.

14. The rivastigmine-containing patch of claim 12, wherein the silicon adhesive is used in an amount of 27 mg/10 cm$^2$ to 33 mg/10 cm$^2$ based on the dry weight of the layer for adhering to the skin.

* * * * *